United States Patent [19]

Sayo et al.

[11] Patent Number: 4,766,227
[45] Date of Patent: Aug. 23, 1988

[54] RUTHENIUM-PHOSPHINE COMPLEX

[75] Inventors: Noboru Sayo, Kanagawa; Takanao Taketomi, Chiba; Hidenori Kumobayashi; Susumu Akutagawa, both of Kanagawa, all of Japan

[73] Assignee: Takasago International Corporation, Tokyo, Japan

[21] Appl. No.: 130,578

[22] Filed: Dec. 9, 1987

[30] Foreign Application Priority Data

Dec. 9, 1986 [JP] Japan .................................. 61-293076

[51] Int. Cl.$^4$ ............................................. C07F 15/00
[52] U.S. Cl. ............................................ 556/21; 556/23
[58] Field of Search ..................................... 556/21, 23

[56] References Cited

U.S. PATENT DOCUMENTS 4,604,474  8/1986  Kumobayashi et al. .......... 556/23 X
4,605,750  8/1986  Kumobayashi et al. .......... 556/23 X
4,691,037  9/1987  Yoshikawa et al. ............... 556/23 X Primary Examiner—Paul F. Shaver
Attorney, Agent, or Firm—Sughrue, Mion, Zinn, Macpeak, and Seas

[57] ABSTRACT

A ruthenium-phosphine complex represented by formula (I):

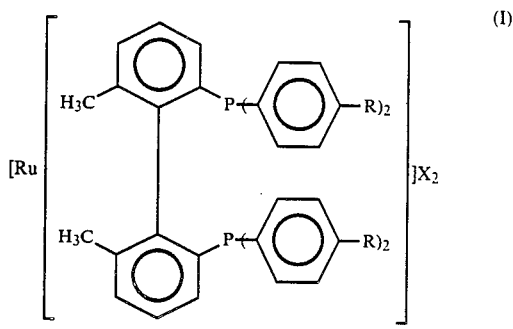

wherein R represents a hydrogen atom, a methyl group, or a methoxy group; and X represents $ClO_4$, $BF_4$, or $PF_6$. The ruthenium-phosphine complex is inexpensive and exhibits excellent performance as a catalyst for various organic syntheses, particularly for asymmetric hydrogenation.

4 Claims, No Drawings

RUTHENIUM-PHOSPHINE COMPLEX

FIELD OF THE INVENTION

This invention relates to a ruthenium-phosphine complex useful as a catalyst for various organic syntheses and asymmetric syntheses, such as asymmetric hydrogenation and asymmetric isomerization.

BACKGROUND OF THE INVENTION

Various organic synthetic reactions using metal complexes have hitherto been developed and utilized for many purposes. In particular, there are a number of reports on asymmetric catalysts to be used in asymmetric syntheses, i.e., asymmetric isomerization, asymmetric hydrogenation, and the like. Of the reported asymmetric catalysts, metal complexes formed between metallic rhodium and an optically active tertiary phosphine are especially well known as catalysts for asymmetric hydrogenation. Such complexes typically include a rhodium-phosphine complex using 2,2'-bis(diphenylphosphino)-1,1'-binaphthyl (hereinafter abbreviated as BINAP) as a ligand as disclosed in Japanese Patent Application (OPI) No. 61937/80 (the term "OPI" as used herein means an "unexamined published Japanese patent application") and a rhodium-phosphine complex using 2,2'-bis(diphenylphosphino)-6,6'-dimethylbiphenyl as a ligand as disclosed in Japanese Patent Application (OPI) No. 65051/84.

On the other hand, known ruthenium-optically active phosphine complexes, though there are not so many reports as compared with rhodium complexes, include those having BINAP or 2,2'-bis(di-p-tolylphosphino)-1,1'-binaphthyl (hereinafter abbreviated as T-BINAP) as a ligand, e.g., $Ru_2Cl_4(BINAP)_2(NEt_3)$ (wherein Et represents an ethyl group, hereinafter the same), $Ru_2Cl_4(T\text{-}BINAP)_2(NEt_3)$, $RuHCl(BINAP)_2$, and $RuHCl(T\text{-}BINAP)_2$, as reported in Ikariya et al., *J. Chem. Soc., Chem. Commun.*, p. 922, (1985). However, the state-of-the-art ruthenium complexes are not satisfactory in stability as well as optical yield attained.

Although metallic rhodium provides excellent complex catalysts, it is expensive due to limitations in place and quantity of production. When used as a catalyst component, it forms a large proportion in cost of the catalyst, ultimately resulting in increase in cost of the final commercial products. While metallic ruthenium is cheaper than rhodium and appears promising as a catalyst component for industrial application, it still has problems in its activity to cope with precision reactions and its range of application. Therefore, it has been keenly demanded to develop a catalyst which is inexpensive, has high activity and durability, and catalyzes asymmetric reactions to attain high optical yields, i.e., to produce reaction products having high optical purity.

SUMMARY OF THE INVENTION

As a result of extensive investigations with the purpose of meeting the above-described industrial demand, the inventors have discovered a novel ruthenium complex having high catalytic activity, which is usable either for general syntheses when the ligand thereof is optically inactive or for asymmetric syntheses when the ligand thereof is optically active. The present invention has been completed based on this finding.

The present invention relates to a ruthenium-phosphine complex represented by formula (I)

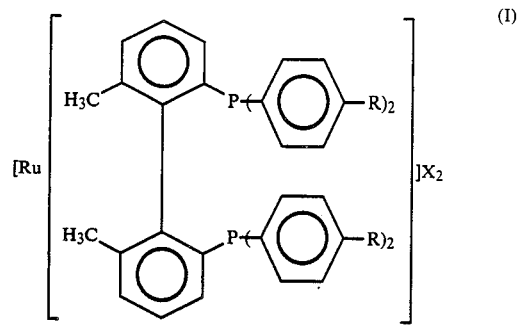

wherein R represents a hydrogen atom, a methyl group, or a methoxy group; X represents $ClO_4$, $BF_4$, or $PF_6$.

DETAILED DESCRIPTION OF THE INVENTION

The 2,2'-bis(diarylphosphino)-6,6'-dimethylbiphenyl as a ligand of the complex of the present invention can be synthesized according to the process reported in Miyashita et al., *The Chemical Society of Japan, Collected Drafts II for Lectures in the 52th Spring Annual Meeting*, IT06, p. 1267 (1986). More specifically, o-toluidine is reacted with nitric acid to form 2-amino-3-methylnitrobenzene, which is then converted to 2-iodo-3-methylnitrobenzene making use of the process described in P. B. Carlin et al., *J. Am. Chem. Soc.*, Vol. 78, p. 1997 (1956). A copper powder is reacted on the resulting product to obtain 2,2'-dinitro-6,6'-dimethylbiphenyl, which is then subjected to hydrogenation using a Raney nickel as a catalyst to obtain 2,2'-diamino-6,6'-dimethylbiphenyl. The product is treated with a 47% hydrobromic acid aqueous solution to obtain 2,2'-dibromo-6,6'-dimethylbiphenyl. A Grignard reagent is prepared from the product according to a process generally employed therefor, for example, by using magnesium. The resulting Grignard reagent is condensed with a diarylphosphinyl chloride selected from diphenylphosphinyl chloride, di-p-tolylphosphinyl chloride, and di-p-anisylphosphinyl chloride to obtain a (±)-2,2'-bis(diarylphosphino)-6,6'-dimethylbiphenyl. The product is resolved by using benzoyl tartrate and then reduced with trichlorosilane to obtain an optically active 2,2'-bis(diarylphosphino)-6,6'-dimethylbiphenyl. Starting with the thus prepared optically active 2,2'-bis(diarylphosphino)-6,6'-dimethylbiphenyl, there can be obtained the ruthenium-phosphine complex of the present invention having the corresponding optical activity.

The ruthenium-phosphine complex of formula (I) according to the present invention can be prepared starting from $Ru_2Cl_4(L)_2NEt_3$ (wherein L represents a 2,2'-bis(diarylphosphino)-6,6'-dimethylbiphenyl, hereinafter the same), which is obtained by reacting $[RuCl_2(COD)]_n$ (wherein COD represents cyclooctadiene, hereinafter the same) and the above-described 2,2'-bis(diarylphosphino)-6,6'-dimethylbiphenyl.

The starting material, $[RuCl_2(COD)]_n$, can be prepared by reacting ruthenium chloride and cycloocta-1,5-diene in an ethanol solvent as taught in M. A. Bennett et al., *Chemistry and Ind.*, p. 1516 (1959). $Ru_2Cl_4(L)_2NEt_3$ can be obtained in a good yield by reacting 1 mole of $[RuCl_2(COD)]_n$, about 1.2 moles of 2,2'-bis(diarylphosphino)-6,6'-dimethylbiphenyl, and about 4 moles of triethylamine in a solvent, e.g., toluene, under heating.

The novel ruthenium-phosphine complex of formula (I) according to the present invention can be prepared by reacting $Ru_2Cl_4(L)_2NEt_3$ with a salt represented by formula (II)

$$MX \qquad (II)$$

wherein X is as defined above; and M represents a metal element selected from Na, K, Li, Mg, and Ag, in a mixed solvent of water and methylene chloride in the presence of, as a phase transfer catalyst, a quaternary ammonium salt or quaternary phosphonium salt represented by formula (III)

$$R^1R^2R^3R^4QZ \qquad (III)$$

wherein $R^1$, $R^2$, $R^3$, and $R^4$ each represents an alkyl group having from 1 to 16 carbon atoms, a phenyl group, or a benzyl group; Q represents a nitrogen atom or a phosphorus atom; and Z represents a halogen atom.

The reaction between $Ru_2Cl_4(L)_2NEt_3$ and the salt of formula (II) is carried out by adding these two reactants and the phase transfer catalyst of formula (III) to a mixed solvent of water and methylene chloride and stirring the mixture. The amount of the salt of formula (II) to be added ranges from 2 to 10 moles, preferably 5 moles, per mole of the ruthenium, and the amount of the phase transfer catalyst of formula (III) ranges from 1/100 to 1/10 mole per mole of the ruthenium. The reaction sufficiently proceeds by stirring at a temperature of from 5° to 30° C. for a period of from 6 to 18 hours, usually 12 hours, while optimum conditions are determined depending on the kinds of the starting complex and the salt of formula (II). As a solvent system, water and methylene chloride are suitably used in approximately equal amounts, and the salt and the phase transfer catalyst are added to the reaction system as dissolved in water.

Examples of the salt of formula (II) to be used include perchlorates, borofluorides, and hexafluorophosphates of Na, K, Li, Mg, or Ag, whose anionic group is introduced into the ruthenium complex.

The phase transfer catalyst of formula (III) which can be used in the present invention include those described in literatures, e.g., W. P. Weber and G. W. Gokel, *Phase Transfer Catalysts in Organic Synthesis*, 1st Ed., Kagaku Dojin (1978), etc. Specific examples of these phase transfer catalysts are quaternary ammonium salts, e.g., tetramethylammonium bromide, tetrapolylammonium bromide, tetrabutylammonium chloride, tetrabutylammonium iodide, octyltrimethylammonium bromide, lauryltrimethylammonium bromide, lauryltriphenylammonium bromide, cetyltrimethylammonium chloride, methyltrioctylammonium chloride, benzyltriethylammonium bromide, etc.; and quaternary phosphonium salts, e.g., tetrabutylphosphonium chloride, tetrabutylphosphonium bromide, tetrabutylphosphonium iodide, lauryltriethylphosphonium bromide, lauryltributylphosphonium bromide, trioctylethylphosphonium bromide, butyltriphenylphosphonium chloride, lauryltributylphosphonium bromide, benzyltributylphosphonium bromide, etc.

After completion of the reaction, the reaction mixture is allowed to stand, followed by liquid separation to remove the aqueous layer. The methylene chloride solution is then washed with water, and the methylene chloride is removed by distillation under reduced pressure to obtain the desired product.

The ruthenium-phosphine complex of formula (I) according to the present invention can also be prepared by starting with $Ru(O_2CCH_3)_2(L)$ as follows. The starting material, $Ru(O_2CCH_3)_2(L)$, is obtained by reacting $Ru_2Cl_4(L)_2NEt_3$ with sodium acetate in an alcohol solvent, e.g., methanol, ethanol, t-butanol, etc., at a temperature of from about 20° to 110° C. for a period of from 3 to 15 hours, removing the solvent by distillation, extracting the desired complex with a solvent, e.g., diethyl ether, ethanol, etc., and then evaporating the extract to dryness. The resulting $Ru(O_2CCH_3)_2(L)$ is then reacted with an acid represented by formula (IV)

$$HX \qquad (IV)$$

wherein X is as defined above, in a mixed solvent of methylene chloride and methanol while stirring. The acid of formula (IV) is used in an amount of from 2 to 6 moles, preferably 4 moles, per mole of the ruthenium. This reaction is carried out at a temperature of from 5° to 30° C. for a period of from 6 to 18 hours, usually 12 hours, while stirring, though the optimum reaction conditions are determined depending on the kind of the acid of formula (IV). The methylene chloride and methanol are suitably used at an approximately equivalent ratio.

Specific examples of the ruthenium-phosphine complexes according to the present invention are shown below.

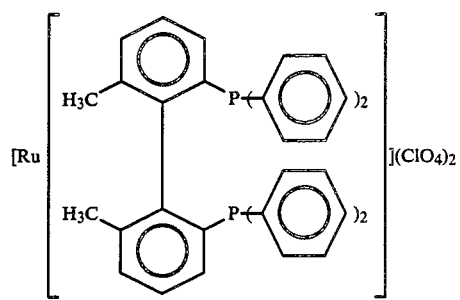

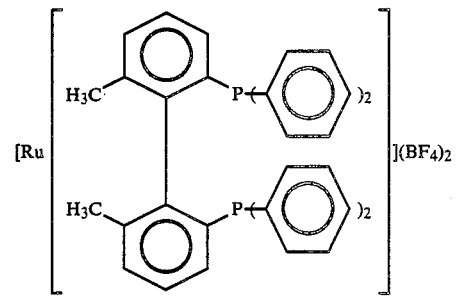

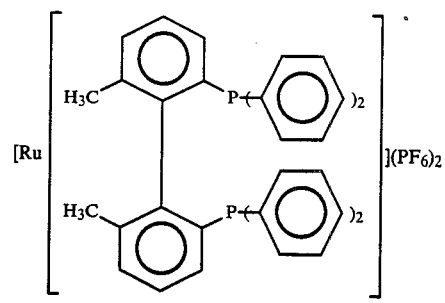

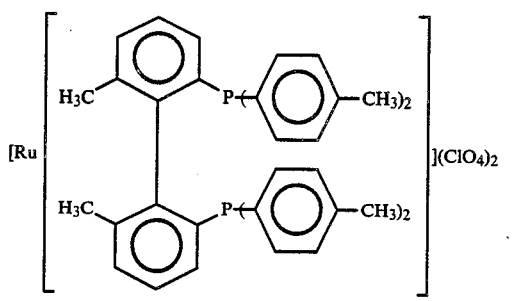

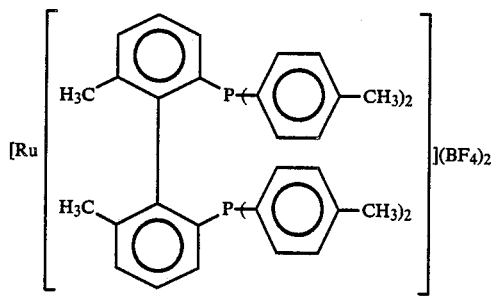

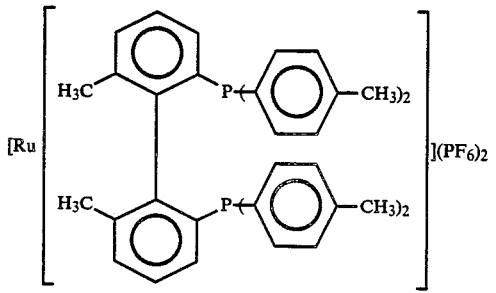

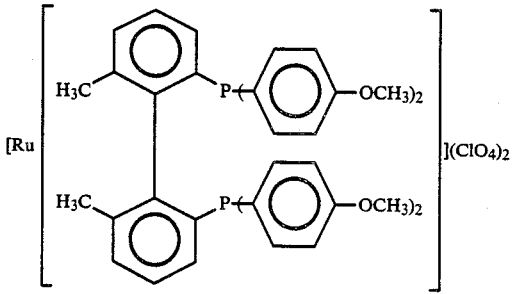

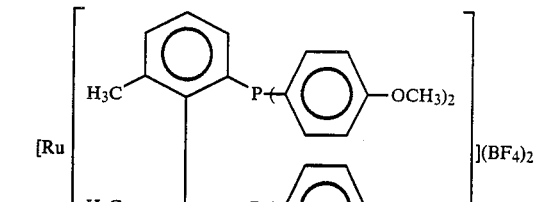

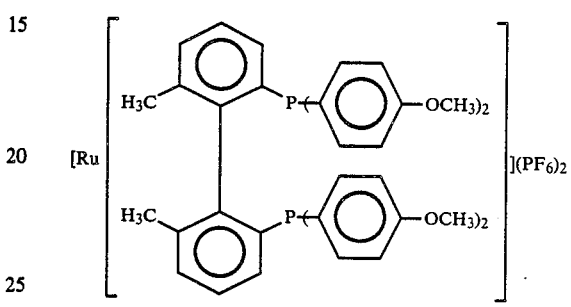

The thus obtained ruthenium-phosphine complex of formula (I) according to the present invention contains a biphenyl basic structure as a ligand that exhibits higher structural flexibility and higher solubilities to various solvents and is, therefore, more applicable to various reactions as compared with a BINAP ligand. The ruthenium-phosphine complex of the invention exhibits excellent performance as a catalyst for asymmetric hydrogenation or the like reaction. For example, when it is applied to asymmetric hydrogenation reaction of α,β-unsaturated carboxylic acids, such as tiglic acid, i.e., (E)-2-methyl-2-butenoic acid, etc., the reaction rapidly proceeds in the presence of the complex of formula (I) at a temperature of from 10° to 50° C. to produce an optically active carboxylic acid derivative, i.e., hydrogenation product, at a selectivity reaching almost 100%. Further, the thus produced carboxylic acid has an optical purity of from 90 to 95%. Thus, the ruthenium-phosphine complexes according to the present invention show very excellent results as industrially useful catalysts.

The present invention will hereinafter be illustrated in greater detail with reference to Reference Examples, Examples, and Use Example, but it should be understood that the present invention is not deemed to be limited thereto.

REFERENCE EXAMPLE 1

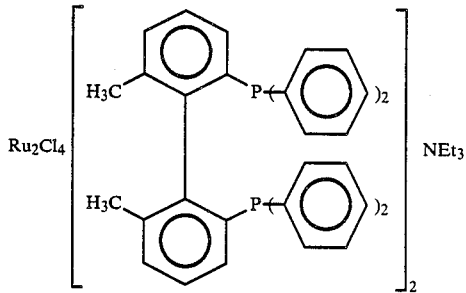

[Bis(μ,μ'-dichloro)bis{2,2'-bis(diphenylphosphino)-6,6'-dimethylbiphenyl}]diruthenium-Triethylamine To 50 ml of toluene were added 0.5 g (1.8 mmoles) of [RuCl₂(COD)]ₙ, 1 g (1.82 mmoles) of 2,2'-bis(diphenylphosphino)-6,6'-dimethylbiphenyl, and 1.0 ml (7.2 mmoles) of triethylamine under a nitrogen atmosphere, and the mixture was stirred while heating under toluene refluxing for 6 hours to effect reaction. The solvent was removed from the reaction mixture by distillation, and the residue was dried under reduced pressure. The solid was dissolved in methylene chloride, followed by filtration through Celite. The filtrate was concentrated to dryness under reduced pressure to obtain 1.35 g of the titled compound as deep red crystals. The yield was 97%.

Elemental Analysis for $C_{82}H_{79}P_4NCl_4Ru_2$: Calcd. (%): Ru 13.07, P 8.01, C 63.69, H 5.15. Found (%): Ru 12.71, P 7.64, C 64.07, H 5.52.

$^{31}P$ NMR (CDCl₃) δ ppm: 51.63 (d, J=40.0 Hz), 52.52 (d, J=41.5 Hz).

$^1H$ (CDCl₃) δ ppm: 1.27 (s, 12H), 1.30 (br. s, 9H), 2.91-3.08 (m, 6H), 6.58-8.18 (m, 52H).

REFERENCE EXAMPLE 2

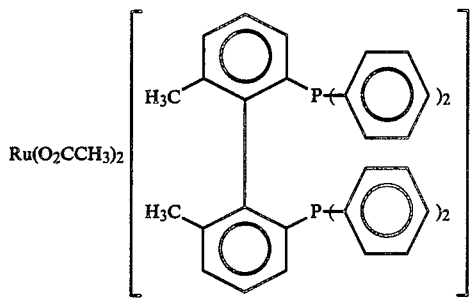

[2,2'-Bis(diphenylphosphino)-6,6'-dimethylbiphenyl]ruthenium-Diacetate

In a 80 ml-volume Schlenk's tube were charged 0.66 g (0.85 mmole) of the [bis(μ,μ'-dichloro)bis{2,2'-bis(diphenylphosphino)-6,6'-dimethylbiphenyl}]diruthenium-triethylamine as prepared in Reference Example 1 and 0.70 g (8.54 mmoles) of sodium acetate. After the atmosphere had been thoroughly displaced with nitrogen, 40 ml of t-butanol was added thereto, followed by heat-refluxing for 14 hours. After completion of the reaction, the t-butanol was removed by distillation under reduced pressure, and the residue was evaporated to dryness and extracted three times with 5 ml portions of diethyl ether. The diethyl ether was removed by distillation to dryness, and the solid was further extracted three times with 5 ml portions of ethanol. The extract was concentrated to dryness to obtain 0.65 g of the titled compound as a yellowish brown solid. The yield was 98.6%.

Elemental Analysis for $C_{42}H_{44}O_4P_2Ru$: Calcd. (%): Ru 13.03; P 7.98; C 65.02; H 5.72. Found (%): Ru 12.69; P 7.78; C 65.41; H 6.08.

$^{31}P$ NMR (CDCl₃) δ ppm: 61.18 (s).

$^1H$ NMR (CDCl₃) δ ppm: 1.32 (s, 6H), 1.72 (s, 6H), 6.61-7.72 (m, 26H).

EXAMPLE 1

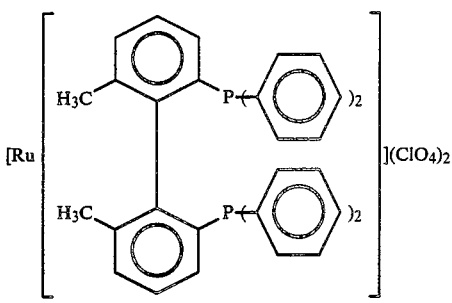

[2,2'-Bis(diphenylphosphino)-6,6'-dimethylbiphenyl]ruthenium-Diperchlorate

In a 250 ml-volume Schlenk's tube was charged 0.23 g (0.3 mmole) of the [bis(μ,μ'-dichloro)bis{2,2'-bis(diphenylphosphino)-6,6'-dimethylbiphenyl}]diruthenium-triethylamine as prepared in Reference Example 1. After the atmosphere had been thoroughly displaced with nitrogen, 60 ml of methylene chloride was added thereto, and a solution of 0.73 g (6.0 mmoles) of sodium perchlorate in 60 ml of water and a solution of 16 mg (0.06 mmole) of triethylbenzylammonium bromide in 3 ml of water were added thereto, followed by stirring at room temperature for 12 hours. After completion of the reaction, the reaction mixture was allowed to stand, followed by liquid separation to remove the aqueous layer. The methylene chloride solution was washed with 50 ml of water, followed by liquid separation. The methylene chloride was removed by distillation under reduced pressure, and the residue dried under reduced pressure to obtain 0.25 g of the titled compound as a deep brown solid. The yield was 98%.

Elemental Analysis for $C_{38}H_{32}Cl_2O_8P_2Ru$: Calcd. (%): Ru 11.88; P 7.28; C 53.66; H 3.79. Found (%): Ru 11.47; P 6.93; C 53.91; H 4.10.

$^{31}P$ NMR (CDCl₃) δ ppm: 46.27 (d, J=47.95 Hz), 69.09 (d, J=47.95 Hz).

EXAMPLE 2

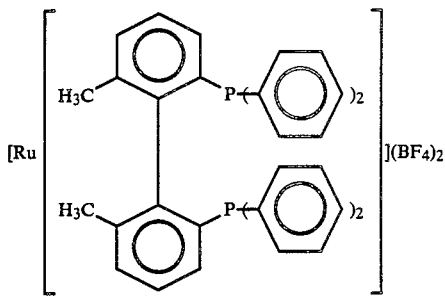

[2,2'-Bis(diphenylphosphino)-6,6'-dimethylbiphenyl]ruthenium-Ditetrafluoroborate In a Schlenk's tube was charged 0.23 g (0.3 mmole) of the [2,2'-bis(diphenylphosphino)-6,6'-dimethylbiphenyl]ruthenium-diacetate as prepared in Reference Example 2. After the atmosphere had been thoroughly displaced with nitrogen, 5 ml of methylene chloride, 5 ml of methanol, and 0.25 ml (1.2 mmoles) of a 42 wt% borofluoric acid were added thereto, followed by stirring at room temperature for 12 hours. The reaction mixture was concentrated under reduced pressure to obtain 0.24 g of the titled compound as a yellowish brown solid. The yield was 97%.

Elemental Analysis for $C_{38}H_{32}B_2F_8P_2Ru$: Calcd. (%): Ru 12.25; P 7.51; C 55.30; H 3.91. Found (%): Ru 11.89; P 7.23; C 55.67; H 4.12.

$^{31}P$ NMR (CDCl$_3$) δ ppm: 46.17 (d, J=47.95 Hz), 69.08 (d, J=47.95 Hz).

EXAMPLE 3

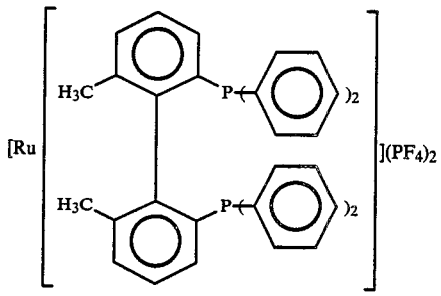

[2,2'-Bis(diphenylphosphino)-6,6'-dimethylbiphenyl]ruthenium-Dihexafluorophosphate In a 250 ml-volume Schlenk's tube was charged 0.23 g (0.3 mmole) of the [bis(μ,μ'-dichloro)bis{2,2'-bis(diphenylphosphino)-6,6'-dimethylbiphenyl}]diruthenium-triethylamine as prepared in Reference Example 1. After the atmosphere had been thoroughly displaced with nitrogen, 60 ml of methylene chloride was added thereto, and subsequently, a solution of 1.10 g (6.0 mmoles) of potassium hexafluorophosphate in 60 ml of water and a solution of 16 mg (0.06 mmole) of triethylbenzylammonium bromide in 3 ml of water were added thereto. The reaction mixture was stirred at room temperature for 12 hours. After completion of the reaction, the reaction mixture was allowed to stand, followed by liquid separation to remove the aqueous layer. The methylene chloride solution was washed with 50 ml of water, followed by liquid separation. The methylene chloride was removed by distillation under reduced pressure, and the residue was dried under reduced pressure to obtain 0.27 g of the titled compound as a deep brown solid. The yield was 96%.

Elemental Analysis for $C_{38}H_{32}F_{12}P_4Ru$: Calcd. (%): Ru 10.76; P 12.94; C 48.60; H 3.43. Found (%): Ru 10.44; P 12.61; C 48.91; H 3.81.

$^{31}P$ (CDCl$_3$) δ ppm: 46.15 (d, J=47.95 Hz), 69.08 (d, J=47.95 Hz).

USE EXAMPLE

Preparation of (2R)-(−)-2-Methylbutyric Acid

In a 300 ml-volume stainless steel autoclave whose atmosphere had been displaced with nitrogen, 1 g (10 mmoles) of (E)-2-methyl-2-butenoic acid and 50 ml of methanol were charged, and 16.5 mg (0.02 mmole) of the [2,2'-bis(diphenylphosphino)-6,6'-dimethylbiphenyl]-ruthenium-ditetrafluoroborate as prepared in Example 2 was added thereto. The mixture was subjected to hydrogenation at 20° C. and at a hydrogen pressure of 4 kg/cm$^2$ for 20 hours. After the completion of the reaction, the solvent was removed by distillation to obtain 1 g of 2-methylbutyric acid. The yield was 100%.

Boiling Point: 50° C./0.07 mmHg.
Optical Rotation: $[α]_D^{23}$ −18.09° (neat).
$^1H$ NMR (CDCl$_3$) δ ppm: 0.95 (t, 3H), 1.17 (d, 3H), 1.15–2.00 (m, 2H), 2.4 (m, H), 9.76 (s, 1H).

The resulting carboxylic acid was reacted with (R)-(+)-1-(1-naphthyl)ethylamine to synthesize an amide compound. High performance liquid chromatography of the amide revealed that the above obtained carboxylic acid comprised 97.2% of (2R)-(−)-2-methylbutyric acid having an optical purity of 94.4% ee and 2.8% of (2S)-(+)-2-methylbutyric acid.

The present invention provides a novel ruthenium-phosphine complex exhibiting excellent performance as a catalyst for various organic syntheses, and particularly asymmetric hydrogenation, and shows industrially superior results in selective hydrogenation of olefins as well as in catalytic activity. Further, the complex according to the present invention can be produced at low cost, making a contribution to reduction of product price and, thus, has a high industrial value.

While the invention has been described in detail and with reference to specific embodiments thereof, it will be apparent to one skilled in the art that various changes and modifications can be made therein without departing from the spirit and scope thereof.

What is claimed is:

1. A ruthenium-phosphine complex represented by formula (I):

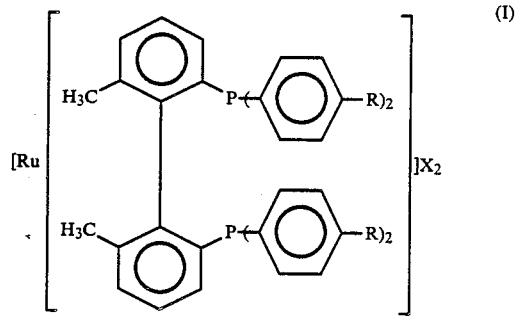

(I)

wherein R represents a hydrogen atom, a methyl group, or a methoxy group; and X represents ClO$_4$, BF$_4$, or PF$_6$.

2. [2,2'-Bis(diphenylphosphino)-6,6'-dimethylbiphenyl]ruthenium-diperchlorate, according to claim 1.

3. [2,2'-Bis(diphenylphosphino)-6,6'-dimethylbiphenyl]ruthenium-ditetrafluoroborate, according to claim 1.

4. [2,2'-Bis(diphenylphosphino)-6,6'-dimethylbiphenyl]ruthenium-dihexafluorophosphate, according to claim 1.

* * * * *